United States Patent [19]
Lewis et al.

[11] Patent Number: 6,115,624
[45] Date of Patent: Sep. 5, 2000

[54] MULTIPARAMETER FETAL MONITORING DEVICE

[75] Inventors: Donald E. Lewis, Monrovia; George D. Park, Arcadia; Randall I. Park, Brea, all of Calif.

[73] Assignee: Genesis Technologies, Inc., Brea, Calif.

[21] Appl. No.: 09/124,935

[22] Filed: Jul. 29, 1998

Related U.S. Application Data

[60] Provisional application No. 60/054,169, Jul. 30, 1997.

[51] Int. Cl.$^7$ .................. A61B 5/0448; A61B 5/0444
[52] U.S. Cl. ............................. 600/376; 600/511
[58] Field of Search .................. 600/511, 376, 600/509, 514

[56] References Cited

U.S. PATENT DOCUMENTS

| | | |
|---|---|---|
| Re. 33,088 | 10/1989 | Jones et al. . |
| 3,599,628 | 8/1971 | Abbenante et al. . |
| 3,621,844 | 11/1971 | Hayashi et al. . |
| 3,703,168 | 11/1972 | Frink . |
| 3,769,984 | 11/1973 | Muench . |
| 3,916,878 | 11/1975 | Courtin et al. . |
| 3,989,034 | 11/1976 | Hojaiban . |
| 4,037,151 | 7/1977 | Takeuchi . |
| 4,211,237 | 7/1980 | Nagel . |
| 4,456,959 | 6/1984 | Hirano et al. . |
| 4,463,425 | 7/1984 | Hirano et al. . |

(List continued on next page.)

FOREIGN PATENT DOCUMENTS

| | | |
|---|---|---|
| 0 306 915 | 3/1989 | European Pat. Off. . |
| 1243692 A1 | 7/1986 | U.S.S.R. . |
| 1461-403-A | 3/1989 | U.S.S.R. . |
| 2 195 897 | 4/1988 | United Kingdom . |

OTHER PUBLICATIONS

Richard H. Paul, M.D. FACOG and Edward H. Hon, M.D. FACOG, "Clinical Fetal Monitoring, IV. Experience with a Spiral Electrode"; Obstetrics Gynecology vol. 41(5), pp. 777–780, May 1973.

H. Bal, N. Exalto, G.E.P.M. van Venrooij, "Intrauterine Detection of Fetal Phonocardiosignals", *Europ. J. Obstet Gynec. Reprod. Biol.*, vol. 8(2), pp. 83–88, 1978.

Lawrence D. Devoe, M.D., Roger P. Smith, M.D. and Ronald Stoker, M.S., "Intrauterine Pressure Catheter Performance in an In Vitro Uterine Model: A Simulation of Problems for Intrapartum Monitoring", Obstetrics & Gynecology, vol. 82(2), pp. 285–289, Aug. 1993.

Thomas H. Strong, et al., "the Intrauterine Probe–Electrode", Dept. of Obstetrics and Gynecology, University of Southern California School of Medicine & Woman's Hospital, Los Angeles Co./USC Medical Center, Los Angeles, CA, pp. 1–19.

*Primary Examiner*—Carl H. Layno
*Attorney, Agent, or Firm*—Lyon & Lyon LLP

[57] ABSTRACT

An intrauterine catheter device for monitoring fetal and/or maternal heart rate, including an elongate housing having proximal and distal portions, an array of ECG electrodes on the distal portion and one or more acoustic or other mechanical sensors on the distal portion. A pressure transducer may also be provided on the distal portion. Processor circuitry compares the ECG signal with the output signal of the acoustic sensor to derive fetal and/or maternal heart rate. An intrauterine catheter device is also provided, including a reference electrode on its distal portion, and an array of active electrodes spaced apart from one another on the distal portion. The device may also include a pressure transducer on the distal portion and processor circuitry coupled to the array of active electrodes and/or to the reference electrode for deriving fetal ECG from signals produced by the array of active electrodes. Alternatively, the array of electrodes and acoustic sensors may be provided on a flexible pad that may be secured to the abdomen of a pregnant mother. An intrauterine catheter device is also provided, including a plurality of lumens communicating with a differential pressure transducer provided on its distal portion, and having a zeroing switch on its proximal portion for resetting the pressure transducer in situ.

31 Claims, 7 Drawing Sheets

U.S. PATENT DOCUMENTS

| | | |
|---|---|---|
| 4,569,356 | 2/1986 | Kyozuka . |
| 4,573,479 | 3/1986 | Tuccillo . |
| 4,781,200 | 11/1988 | Baker . |
| 4,785,822 | 11/1988 | Wallace . |
| 4,873,986 | 10/1989 | Wallace . |
| 4,898,179 | 2/1990 | Sirota . |
| 4,945,917 | 8/1990 | Aksezrod et al. . |
| 4,949,730 | 8/1990 | Cobben et al. . |
| 4,951,680 | 8/1990 | Kirk et al. . |
| 4,966,152 | 10/1990 | Gang et al. . |
| 4,967,761 | 11/1990 | Nathanielsz . |
| 4,989,615 | 2/1991 | Hochberg . |
| 5,025,787 | 6/1991 | Sutherland et al. ............... 600/376 |
| 5,042,499 | 8/1991 | Frank et al. . |
| 5,042,503 | 8/1991 | Torok et al. . |
| 5,070,888 | 12/1991 | Hon et al. . |
| 5,109,849 | 5/1992 | Goodman et al. . |
| 5,123,420 | 6/1992 | Paret . |
| 5,140,992 | 8/1992 | Zuckerwar et al. . |
| 5,184,619 | 2/1993 | Austin ............... 600/376 |
| 5,295,486 | 3/1994 | Wollschlager et al. . |
| 5,425,362 | 6/1995 | Siker et al. . |
| 5,807,271 | 9/1998 | Tayebi et al. ............... 600/511 |

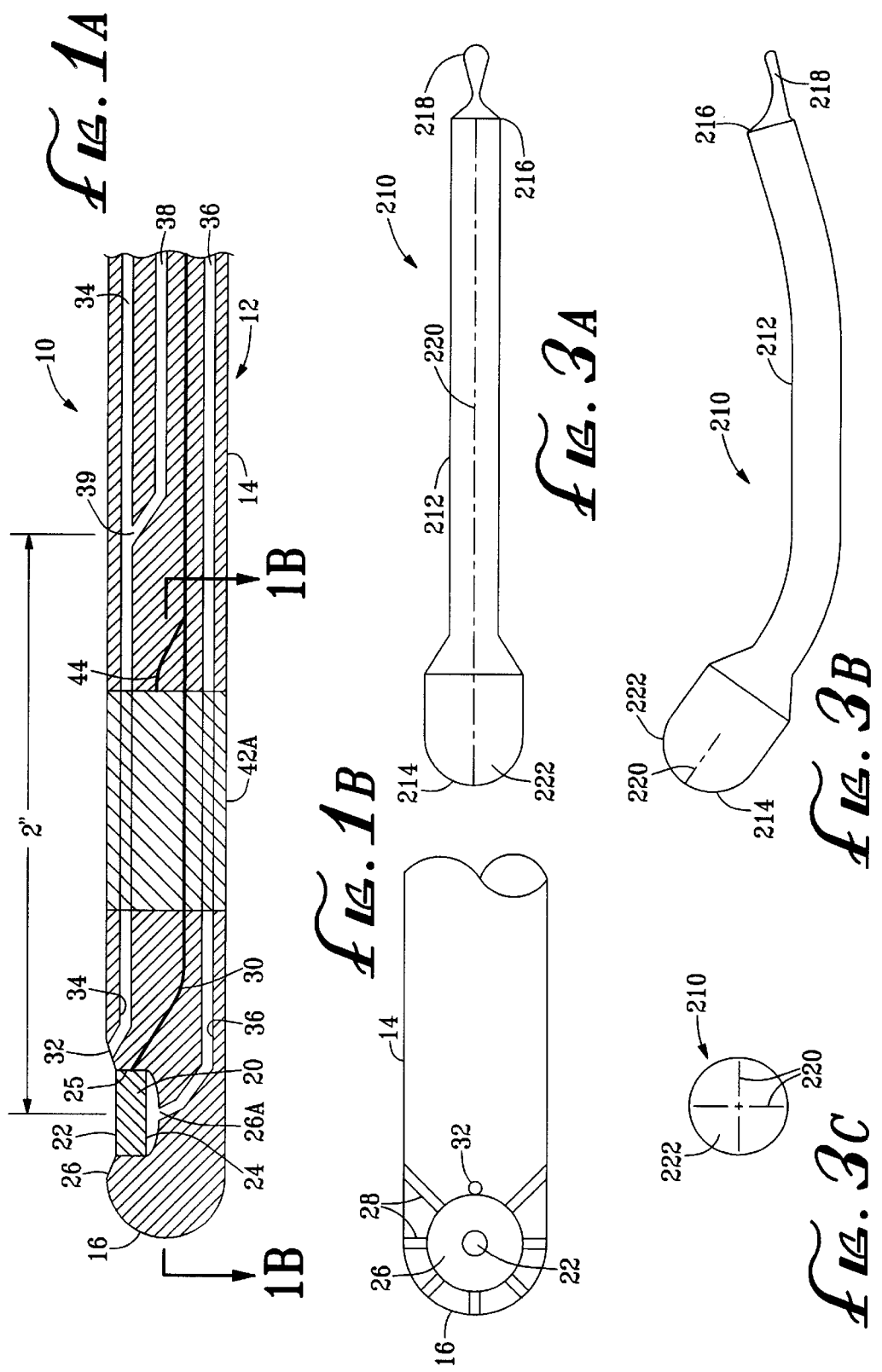

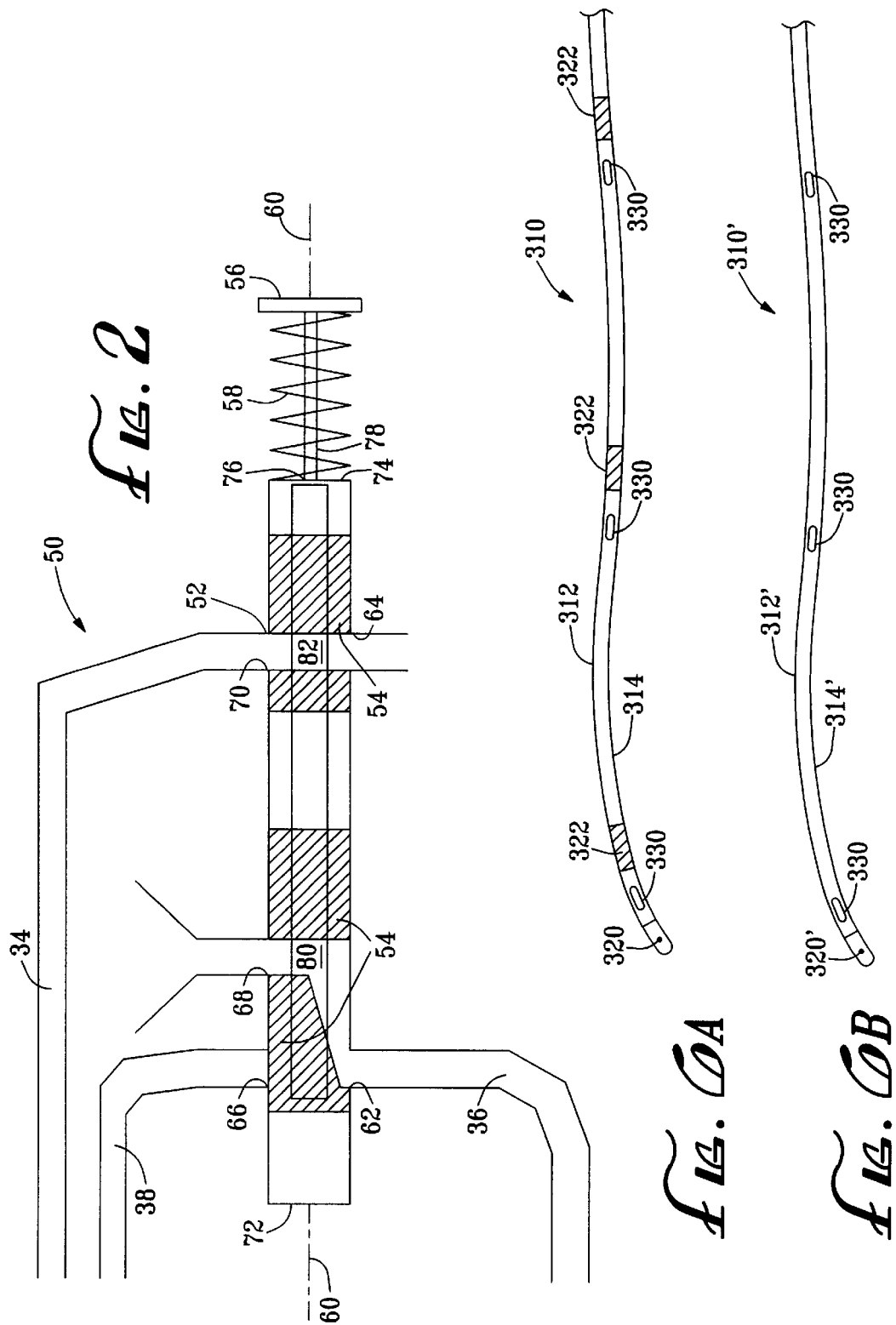

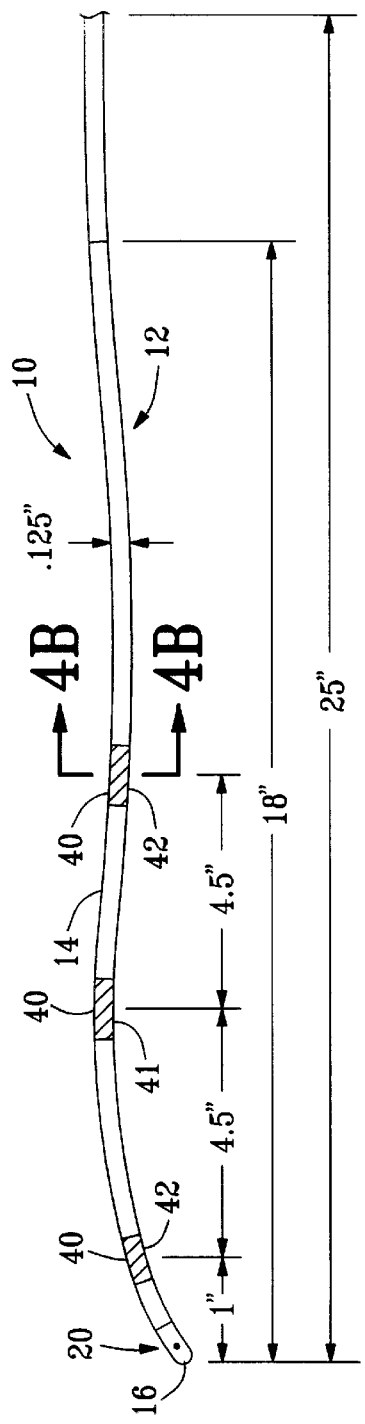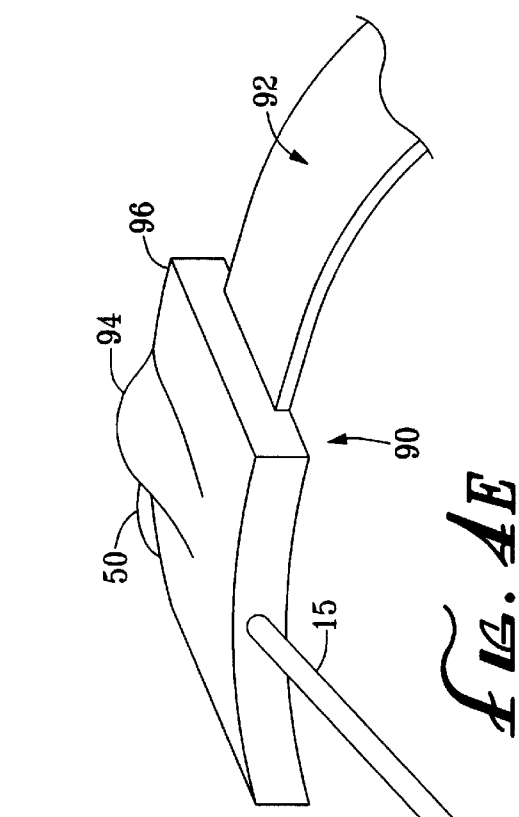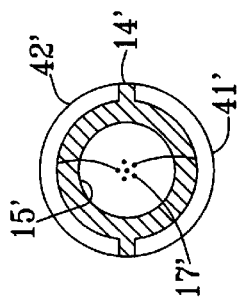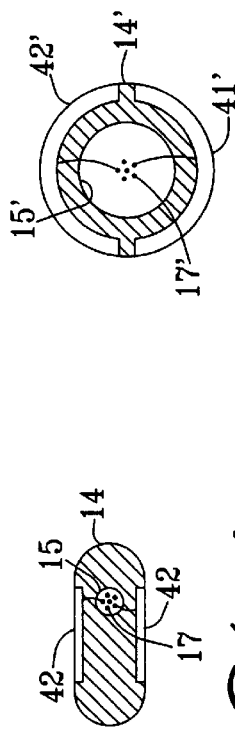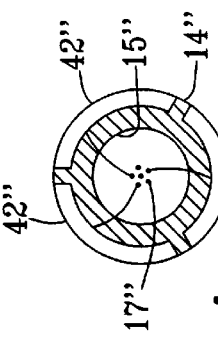

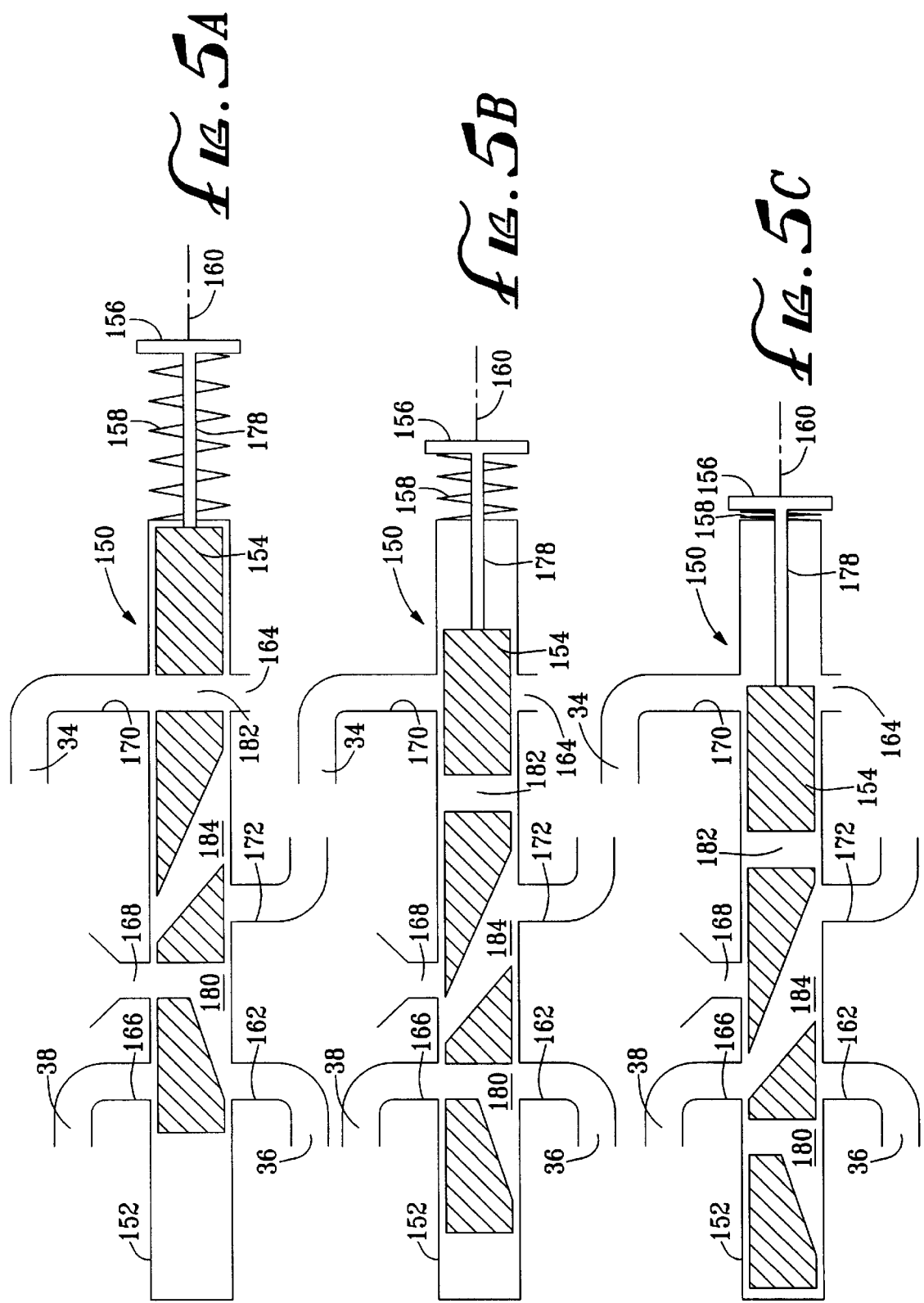

MULTIPARAMETER FETAL MONITORING DEVICE

This application claims the benefit of U.S. Provisional Application Ser. No. 60/054,169, filed Jul. 30, 1997, the disclosure of which is expressly incorporated herein by reference.

FIELD OF THE INVENTION

The present invention relates generally to devices and methods for monitoring a fetus and/or the fetus' mother during pregnancy, labor and childbirth, and more particularly to intrauterine pressure, fetal heart rate and/or maternal heart rate sensors that are noninvasive to the fetus.

BACKGROUND

A variety of devices are available for separately monitoring intrauterine pressure and fetal heart rate of a pregnant mother and her fetus during pregnancy or labor. For example, to measure uterine contractions an external transducer diaphragm may be provided that is secured to the mother's abdomen by a belt or other device. During labor, contractions and/or intrauterine pressure may be sensed by the transducer diaphragm and displayed on a monitoring device. Such external devices, however, may be awkward to use, may slip and/or lose effective contact with the mother's abdomen, potentially resulting in less accurate uterine contraction information.

To monitor fetal heart rate, devices that are invasive to the fetus have been used to sense the fetal ECG from which the heart rate may be obtained. Such devices are generally positively fixed to the fetus, for example, by a harpoon tip or a corkscrew-type electrode, which are anchored or screwed into the scalp of the fetus. Alternatively, a suction cup device may be attached to the head of the fetus that includes a sensor therein. Such devices, however, generally require direct contact with the fetus, and often also require penetration of the fetus' skin, which may increase the risk of infection or other harm to the fetus.

More recently, devices have been developed which allow sensing of both pressure and fetal ECG in a single device. For example, U.S. Pat. No. 5,184,619 discloses a device having a pressure transducer and an array of electrodes spaced axially along the device for sensing fetal ECG. The device includes a tubular housing having a distal portion adapted for insertion into a woman's uterus and for placement adjacent to a fetus therein. Two or more electrodes are mounted along the distal portion spaced axially apart from one another, and a pressure transducer is also provided on the distal portion.

Preferably, the pressure transducer is a solid state differential pressure transducer with one side exposed for contacting fluid within the uterus. The other side of the pressure transducer is vented to atmosphere by a lumen extending to a proximal end of the housing. Cables from the electrodes also extend to the proximal end, where they may be connected to processor circuitry and/or a monitoring device which may display fetal ECG or heart rate.

Such devices generally include an external ground or reference electrode placed in contact with the mother's body, e.g., using a leg plate or an external ECG electrode. The reference electrode may facilitate the processor circuitry associated with the monitoring device in separating noise and other signals sensed by the electrode array from the fetal ECG signal. Even with the external reference electrode, the processor circuitry must perform complicated algorithms in order to obtain an accurate fetal ECG and/or fetal heart rate.

Accordingly, there is a need for an intrauterine pressure transducer, fetal ECG and/or fetal heart rate sensor that facilitates monitoring of a fetus, that is more convenient to use, and/or that is noninvasive to the fetus.

SUMMARY OF THE INVENTION

The present invention is directed to devices and methods for monitoring a fetus and/or the fetus' mother. In one aspect of the present invention, an intrauterine catheter device is provided for monitoring fetal heart rate during labor. The catheter device includes an elongate housing having a proximal portion and a distal portion adapted for insertion into a pregnant mother's uterus. An array of electrodes is provided on the distal portion adapted to produce an ECG signal corresponding to ECG activity within the mother's uterus, and one or more mechanical sensors are also provided on the distal portion, the mechanical sensor(s) being adapted to produce an output signal including a fetal heart rate signal. The array of electrodes may include electrodes that may be spaced apart axially along the distal portion and/or may be provided back-to-back from one another, preferably in pairs.

In a preferred form, the mechanical sensor(s) is an acoustic sensor, although alternatively the mechanical sensor(s) may include a micro-gyroscope or a micro-accelerometer. One or more pressure transducers may also be provided on the distal portion for measuring intrauterine pressure. One or more connectors may be provided on the proximal portion coupled to the array of electrodes, the mechanical sensor(s), and/or the pressure transducer(s). Processor circuitry may also be provided, that may be connectable to the connectors for comparing the ECG signal to the output signal of the mechanical sensor to derive fetal heart rate information.

In an alternative embodiment, a device for monitoring fetal heart rate may be provided that includes an array of electrodes spaced apart from one another, one or more acoustic sensors adjacent to the array of electrodes, and processor circuitry for comparing an ECG signal produced by the array of electrodes with an acoustic signal produced by the acoustic sensor(s) to derive fetal heart rate information. The device may include a pad having a lower surface that may be applied to the abdomen of a pregnant mother before or during labor, with the array of electrodes and the acoustic sensor(s) being located on the lower surface of the pad.

The device, with an array of electrodes and one or more acoustic sensors, may be used in a method for deriving fetal heart rate of a fetus in a pregnant mother's uterus during labor. The device may be placed adjacent the fetus, for example against the pregnant mother's abdomen or inserted into her uterus. Fetal and/or maternal ECG activity may be detected within the uterus with the array of electrodes, the array of electrodes producing an ECG signal corresponding to the ECG activity, preferably the combined ECG activity of the mother and fetus. Substantially simultaneously, acoustic activity may be detected with the acoustic sensor(s), the acoustic sensor(s) producing an acoustic signal corresponding to the acoustic activity. The ECG signal and acoustic signal may then be compared by processor circuitry to derive the fetal heart rate and/or the maternal heart rate, which may then be displayed on a video display or other monitoring device. This use of acoustic data in conjunction with ECG data is an important feature of the present invention which may enhance monitoring of fetal and/or maternal heart rate information as compared with the use of acoustic or ECG data alone.

In another aspect of the present invention, an intrauterine catheter device is provided for monitoring a fetus during labor that includes an elongate housing having a proximal portion and a distal portion adapted for insertion into a pregnant mother's uterus, one or more reference electrodes on the distal portion, and an array of active electrodes spaced apart from one another on the distal portion. Preferably, the array of active electrodes includes one or more bipolar pairs of electrodes that are spaced apart axially from one another, for example, about nine inches. In addition, one or more pairs of electrodes may be provided back-to-back from one another, for example, on opposite sides of a substantially flat distal portion, preferably about 0.125–0.25 inch apart. The device may also include one or more pressure transducers on the distal portion and/or one or more mechanical sensors. In addition, the device may include processor circuitry coupled to the array of active electrodes and/or to the reference electrode(s) for deriving fetal ECG and/or fetal heart rate from signals produced by the array of electrodes.

In still another aspect of the present invention, an intrauterine catheter device is provided for monitoring a fetus during labor that includes an elongate housing having a proximal portion and a distal portion adapted for insertion into a pregnant mother's uterus, and including first and second lumens extending between the proximal and distal portions. A differential pressure transducer is provided on the distal portion, the transducer having a front side exposed on the distal portion, and a back side disposed within the distal portion such that the first and second lumens communicate with the front and back sides, respectively. A zeroing switch is provided on the proximal portion of the housing, the zeroing switch being adjustable between first and second positions. In the first position, the second lumen is in communication with external atmospheric pressure, while, in the second position, the second lumen is in communication with the first lumen, to facilitate in situ zeroing of the pressure transducer.

The catheter device may include an array of acoustic sensors on the distal portion and/or an array of ECG electrodes spaced apart from one another on the distal portion. The catheter device may also include a third lumen extending between the proximal and distal portions, the third lumen being connected to the first lumen at a location proximate to the front side of the pressure transducer. The zeroing switch may be adjustable to a third position such that the first lumen is in communication with a port on the zeroing switch, the port being connectable to a source of pressure for forcing fluid from the first lumen.

Other objects and features of the present invention will become apparent from consideration of the following description taken in conjunction with the accompanying drawings.

BRIEF DESCRIPTION OF THE DRAWINGS

FIG. 1A is a cross-sectional view of a distal portion of an intrauterine catheter device in accordance with one aspect of the present invention.

FIG. 1B is a top view of the distal portion of the catheter device of FIG. 1A.

FIG. 2 is a cross-sectional schematic view of a zeroing switch for a catheter device, such as that shown in FIG. 1A, in accordance with another aspect of the present invention.

FIG. 3A is a side view of a peel-away guide tube for an intrauterine catheter device.

FIG. 3B is another side view of the peel-away guide tube of FIG. 3A.

FIG. 3C is an end view of the distal portion of the peel-away guide tube of FIG. 3A.

FIG. 4A is a side view of a catheter device having a pressure sensor and an array of electrodes.

FIG. 4B is a cross-sectional view of the catheter device of FIG. 4A, taken along line B—B.

FIGS. 4C and 4D are cross-sectional views of alternative embodiments of the catheter device of FIG. 4A, taken along line B—B.

FIG. 4E is a perspective view of a platform to which the catheter device of FIG. 4A may be connected, including a zeroing switch and connectors for coupling to a monitoring device.

FIGS. 5A–5C are cross-sectional schematic views of an alternative embodiment of a zeroing switch.

FIGS. 6A and 6B are side views of an alternative embodiment of a catheter device having an array of mechanical sensors thereon, with and without an array of ECG electrodes, respectively.

DETAILED DESCRIPTION OF THE PREFERRED EMBODIMENTS

Figure 7A:
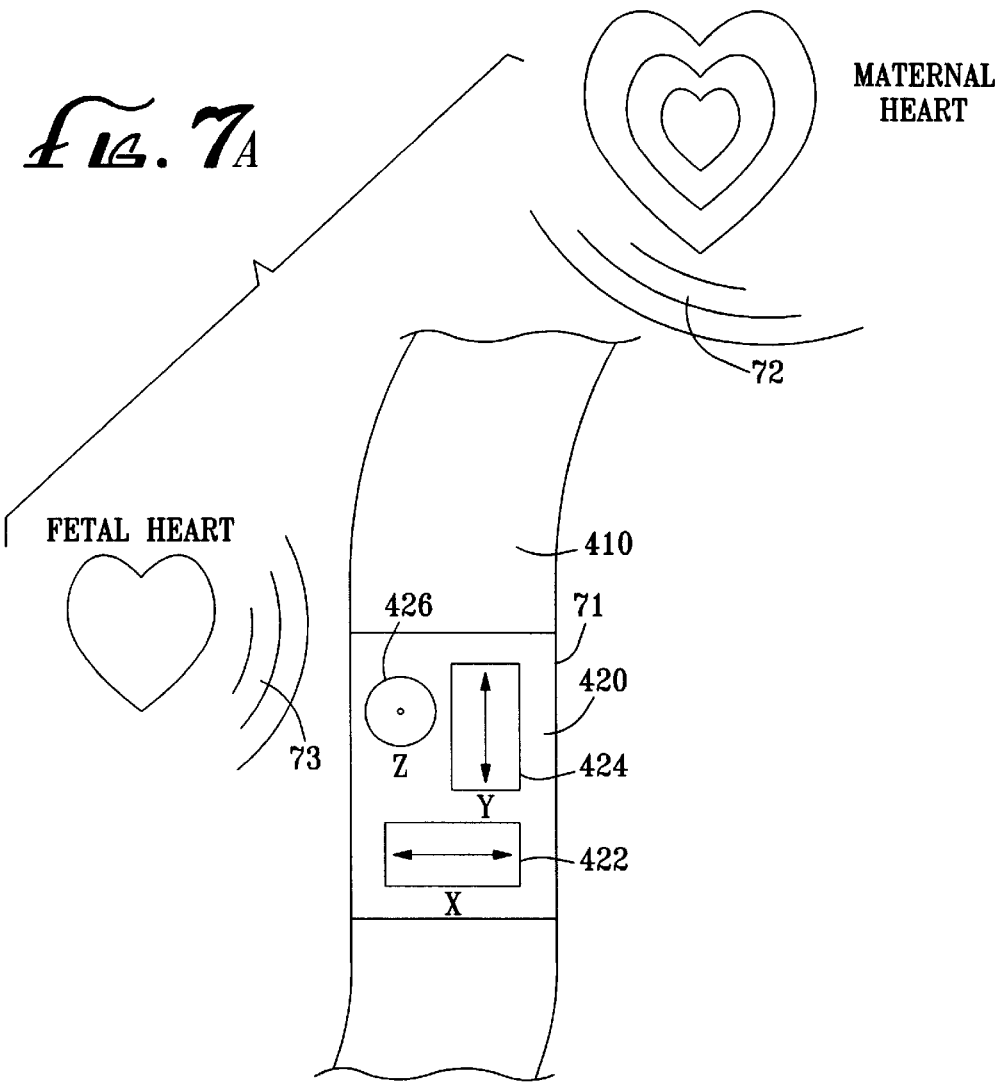
FIG. 7A is a schematic view of an accelerometer sensor for monitoring fetal and maternal heart rates, shown in spatial relation to maternal and fetal hearts.

Turning now to the drawings, FIGS. 1A, 1B, 4A and 4B show an intrauterine catheter device 10 for monitoring a fetus during labor in accordance with one aspect of the present invention. The catheter device 10 includes an elongate tubular housing 12, a pressure transducer 20 and an array of electrodes 40 for monitoring fetal and/or maternal ECG. The housing 12 has a proximal portion (not shown) that may include connectors for coupling to processor circuitry, a video display and/or other monitoring device (not shown), and a distal portion 14 adapted for insertion into a patient's uterus.

The housing 12 may have a substantially cylindrical (see FIGS. 4C and 4D), elliptical or flat cross-section (see FIG. 4B), and may be substantially flexible to facilitate insertion along the birth canal of a pregnant mother (not shown) during labor. Preferably, the housing 12 has a substantially rounded distal tip 16 to facilitate insertion in a nonintrusive manner that minimizes harm to the mother and/or fetus during placement in the uterus.

With particular reference to FIGS. 4A and 4B, the array of electrodes 40 includes a common or reference electrode 41 and an array of active electrodes 42 for monitoring fetal and/or maternal ECG or heart rate. Preferably, the active electrodes 42 are spaced apart axially from one another about nine inches and are provided in back-to-back pairs, each of which may be coupled into bipolar pairs by cables 17 extending along a lumen 15 to the proximal portion of the catheter device 10. The reference electrode 41 is preferably centered between the active electrode pairs 42 and also includes one or more cables 17 for coupling the reference electrode 41 to processor circuitry and/or a monitoring device, as described further below. Alternatively, multiple bipolar pairs of electrodes may be included in the array, a plurality of unipolar electrodes may be provided and/or a plurality of reference electrodes may be included. In a further alternative, shown in FIG. 4D, active electrodes 42" may be provided in back-to-back pairs adjacent to a local reference electrode 41".

The electrodes 41, 42 may be formed from a variety of conductive materials, such as gold, platinum, stainless steel and the like, that are generally safe to introduce within a human body. The electrodes 41, 42 may also have a variety of shapes, such as cylindrical bands, helical coils, curved plates and the like. In a presently preferred form, the electrodes 41, 42 may be 0.5 inch long half bands formed from 0.014 inch thick stainless steel plated with 99.9% pure gold.

Any of the bipolar pairs of electrodes 42 may be used to measure a relatively small differential voltage across the respective pair, the resulting voltage signal including fetal ECG and/or maternal ECG components. Because the catheter device 10 and the patient together create an electrical system, a potential difference exists between the point of measurement, i.e., within the uterus of the patient, and the catheter device 10. This potential difference may be as large or larger than the voltages being measured by the active electrodes 42. The reference electrode 41 substantially ties the reference point of the catheter device 10 to the patient such that both the patient and the catheter device 10 have the same common mode reference.

When tying two points together, it may be useful to tie a common point very close to each point of measurement to the reference of the measuring device. Stated differently, it may be useful to place the reference electrode 41 in close proximity to the active electrodes 42 on the catheter device 10. This arrangement may allow any potential difference between the patient and the catheter device 10 to be seen as a common mode voltage, thereby increasing the signal-to-noise ratio (noise immunity) of the catheter device 10. Thus, providing an internal reference electrode 41, rather than an external reference such as a leg plate, substantially reduces the risk of converting the common mode noise to differential noise which may decrease the signal-to-noise ratio.

Turning particularly to FIG. 1A, the pressure transducer 20 is mounted across a cavity 25 in the distal portion 14 adjacent the distal tip 16, or alternatively elsewhere on the distal portion 14. Preferably, the pressure transducer 20 is a solid state differential pressure transducer including internal temperature compensation components (not shown) and having a front side 22 and a back side 24. The pressure transducer 20 may measure pressures between about 0 mm Hg and about 300 mm Hg, and more preferably between about 0 mm Hg and 100 mm Hg. One or more cables 30 are coupled to the pressure transducer 20 and extend proximally through the housing 12 for coupling the pressure transducer 20 to external electronic circuitry or monitoring equipment (not shown).

The distal portion 14 may include a depression 26 surrounding the cavity 25 and a plurality of channels 28 in communication with the depression 26 for directing uterine fluid into contact with the front side 22 of the pressure transducer 20 to enhance measurement of intrauterine pressure.

A flush port 32 communicating with a first or flush lumen 34 may also be provided adjacent the depression 26 for flushing the front side 24 of the pressure transducer 20 to clear debris that may occlude or otherwise interfere with the operation of the pressure transducer 20. The flush port 32 may also allow a pool of fluid to be delivered into the depression 26 from an external source through the flush lumen 34 to enhance the performance of the pressure transducer 20. The flush lumen 34 may also facilitate infusion of fluid into the uterus for clinical indications and/or facilitate sampling of amniotic fluid for clinical indications. Alternatively, the flush port 32 and flush lumen 34 may be provided on a catheter device that does not include a pressure transducer (not shown).

The back side 24 of the pressure transducer 20 is exposed within a lower portion 25a of the cavity 25. A second or atmosphere lumen 36 extends proximally from the lower portion 25a of the cavity 25 to the proximal portion of the catheter device 10 for providing atmospheric pressure to the back side 24 of the pressure transducer 20, as described more particularly below.

Within the housing 12, a third or zeroing lumen 38 is also provided in addition to the flush and atmosphere lumens 32, 36. The zeroing lumen 38 is connected to the flush lumen 32 in the distal portion 14 at a point 39 near the flush port 32, preferably about two inches from the pressure transducer 20. Alternatively, the zeroing lumen 38 and/or the flush lumen 32 may be eliminated, and the atmosphere lumen 36 may be vented directly to the atmosphere.

Preferably, the atmosphere and zeroing lumens 36,38 have a cross-section substantially smaller than the flush lumen 34, preferably approximately half of the cross-section of the flush lumen 34. The smaller cross-section may substantially reduce the chance of fluid from the flush lumen 34 entering the zeroing lumen 38 and particularly passing through the zeroing lumen 38 into the atmosphere lumen 36. Fluid in the zeroing and/or atmosphere lumens 38, 36 may distort pressure readings obtained using the pressure transducer 20.

Turning to FIGS. 1A and 2, the proximal portion of the housing 12 and/or the three lumens 32, 36, 38 of the catheter device 10 may be connected to a zeroing switch 50 to facilitate resetting the pressure transducer 20 during use in accordance with another aspect of the present invention. The zeroing switch 50 includes an outer sleeve 52, an internal plunger 54 slidable within the outer sleeve 52 between a first position (shown in FIG. 2) and a second position (not shown), a switch 56 for directing the plunger 54, and a spring 58 or other biasing mechanism for biasing the plunger 54 towards the first position.

The outer sleeve 52 is an elongate tubular member, preferably having a cylindrical shape, that defines a longitudinal axis 60 between its first and second ends 72, 74. The first end 72 is substantially closed, while the second end 74 includes an opening 76 through which a stem 78 connected to the switch 56 may extend. A plurality of ports are provided at predetermined locations on the periphery of the outer sleeve 52, and include an atmosphere lumen port 62, a flush port 64, a zero lumen port 66, an atmosphere port 68 and a flush lumen port 70.

The plunger 54 is an elongate member having a shape similar to the interior of the outer sleeve 52 such that the plunger may axially slide within the outer sleeve 52 with substantially minimal lateral movement. The plunger 54 has a plurality of passages extending substantially laterally therethrough, including an atmosphere/zeroing passage 80 and a flush passage 82. The passages 80, 82 have predetermined shapes and locations corresponding to the predetermined locations of the ports 62–70 on the outer sleeve 52. The plunger 54 and/or outer sleeve 52 may also include one or more seals (not shown) to provide a substantially fluidtight seal between the plunger 54 and the outer sleeve 52, and more specifically between the ports 62–70 and the passages 80, 82.

During normal operation, the plunger 54 is generally in the first position, as shown in FIG. 2. In the first position, the atmosphere/zeroing passage 80 allows communication between the atmosphere lumen port 62 and the atmosphere port 68, and the flush passage 82 allows communication between the flush port 64 and the flush lumen port 70. When the switch 56 is depressed, the plunger moves to the second position in which the atmosphere/zeroing passage 80 now allows communication between the zero lumen port 66 and the atmosphere lumen port 62, and the flush lumen port 70 is closed.

The zeroing switch 50 may be attached or otherwise provided on the proximal portion of the catheter device 10 such that the atmosphere lumen, zero lumen and flush lumen ports 62, 66, 70 are connected to and communicate with the atmosphere, zero and flush lumens 36, 38, 34, respectively. When the plunger 54 is in the first position, the zeroing switch 50 allows the atmosphere lumen 36 of the catheter device 10 to receive atmospheric pressure through the atmosphere port 68 via the atmosphere/zeroing passage 80. Thus, atmospheric pressure may be provided on the back side 24 of the pressure transducer 20. In addition, a source of fluid (not shown) may be connected to the flush port 64 and directed through the flush lumen 34, thereby facilitating flushing of the front side 22 of the pressure transducer 20 without having to remove the entire catheter device 10 from the patient.

In the second position, the atmosphere lumen 36 is in communication with the zero lumen 38 via the atmosphere zeroing passage 80. This causes the pressure in the zero lumen 38 and the atmosphere lumen 36 to equalize substantially. Because the zero lumen 38 is connected to the flush lumen 34, the equalized pressure is communicated from the flush port 32 and consequently from the front side 22 of the pressure transducer 20 to the back side 24. With substantially equalized pressure on both the front and back sides 22, 24 of the pressure transducer 20, a substantially zero pressure signal may be produced by the pressure transducer 20, which may be used to reset the processor circuitry and/or monitoring device. Thus, the zeroing switch 50 may facilitate resetting of the pressure transducer 20 in situ within the uterus, thereby substantially compensating for the effects of drift and the like that may be encountered during use.

In an alternative embodiment, shown in FIGS. 5A–5C, a three position switch 150 is provided that includes an outer sleeve 152 and a plunger 154 slidably received therein. The plunger 154 may be advanced between first and second positions, shown in FIGS. 5A and 5B, respectively, similar to the switch 50 shown in FIG. 2. In the first position, an atmosphere/zeroing passage 180 allows communication between an atmosphere lumen port 162 and an atmosphere port 168, and a flush passage 182 allows communication between a flush lumen port 170 and a flush port 164. In the second position, the atmosphere/zeroing passage 180 allows communication between the atmosphere lumen port 162 and a zero lumen port 166, and the flush lumen port 170 is closed.

Unlike the two position switch of FIG. 2, however, the switch 150 also includes a pressure port 172 in the outer sleeve 152 and a pressure passage 184 extending substantially laterally through the plunger 154, and the plunger 154 may be advanced to a third position, shown in FIG. 5C. In the third position, the atmosphere lumen and flush lumen ports 162, 170 are closed, and the zero lumen port 166 communicates with the pressure port 172 through the pressure passage 184. Preferably, the pressure port 172 is connected to a source of pressure, for example, a syringe filled with air, for delivering pressure into the zero lumen port 166 and into the zero lumen 38.

For example, with reference also to FIG. 1A, when the pressure transducer 20 is zeroed, i.e., when the plunger 154 is directed to the second position, fluid from the flush lumen 34 may enter the zero lumen 38 at the point 39 near the flush port 32 because of higher than atmospheric intrauterine pressure that may be encountered at the flush port 32. Once the pressure transducer 20 is zeroed, the plunger 154 may be depressed to the third position, and pressure from the source of pressure connected to the pressure port 172 may be used to force any fluid that has entered the zero lumen 38 back into the flush lumen 34 and/or out the flush port 32.

Turning to FIG. 4E, a zeroing switch 50, such as that shown in FIG. 2 or 5A–5C, may be incorporated into a stable platform or body 90 which may be attachable to the patient, for example, by a set of straps 92 to the patient's leg. A proximal end 15 of a catheter device 10, such as that previously described, may be attached to the platform 90. The platform 90 may include internal lumens or tubing (not shown) to connect the lumens (not shown) of the catheter device 10 to the respective ports (not shown) on the zeroing switch 50. The platform 90 may also include a flush port 96 to which a source of fluid (not shown) may be attached. In addition, the platform 90 may include one or more connectors 94 coupled to the cables (not shown) in the catheter device 10 that extend from the pressure transducer 20 and/or the array of electrodes 40 (see FIG. 1A).

Figure 8:
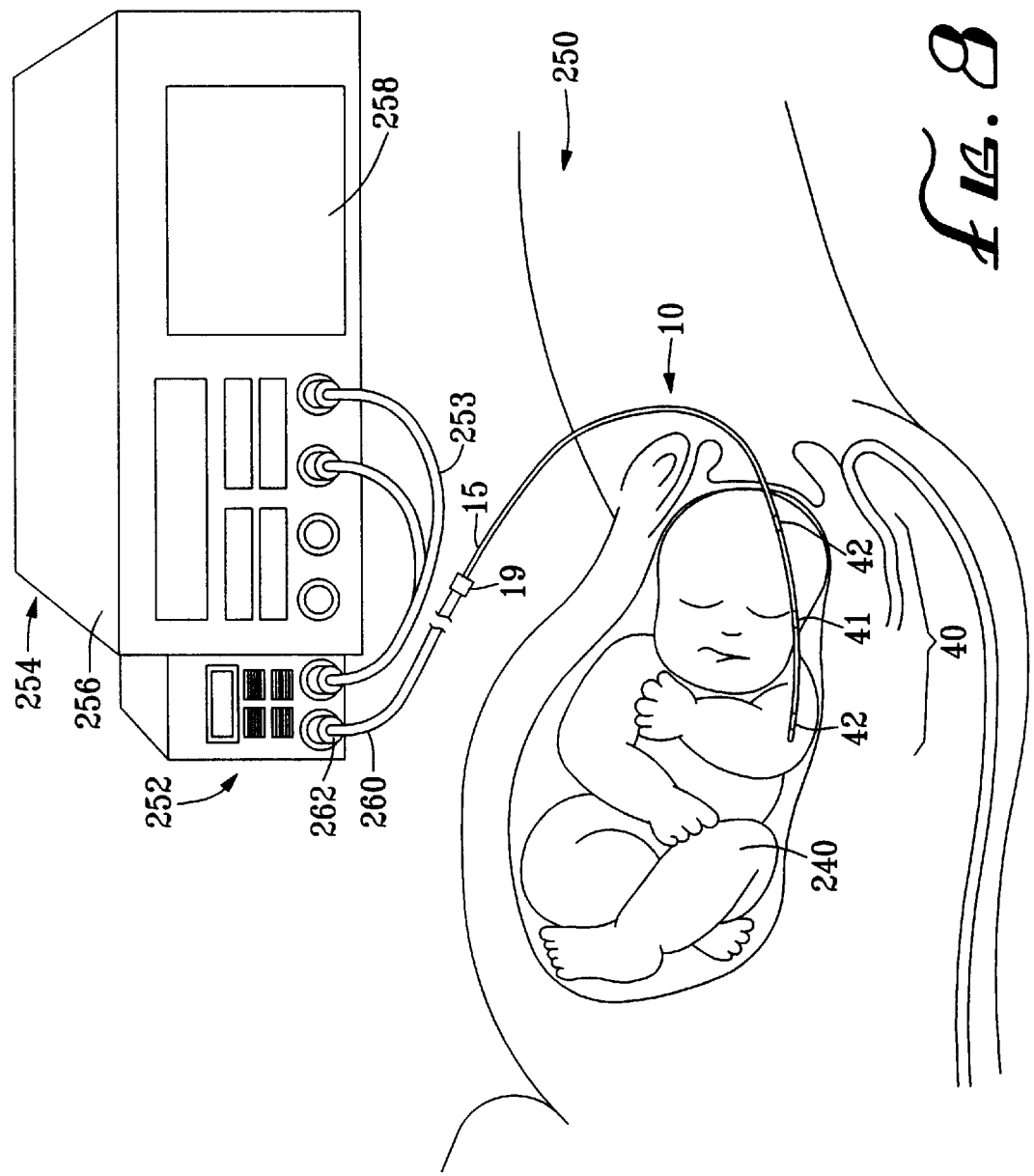
FIG. 8 is a perspective view of a system for monitoring a fetus in utero during labor, including an intrauterine catheter device, a processor box, and a monitoring device.
Figure 9:
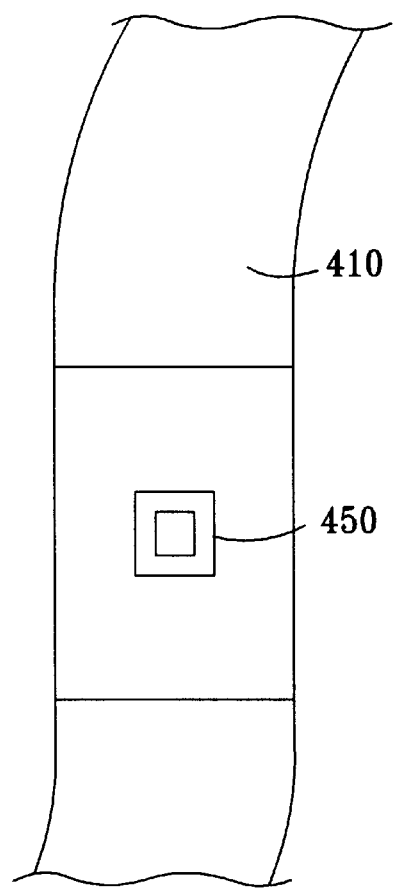
FIG. 9 is a schematic view of a micro-gyroscope for monitoring fetal and maternal heart rates.
Figure 10:
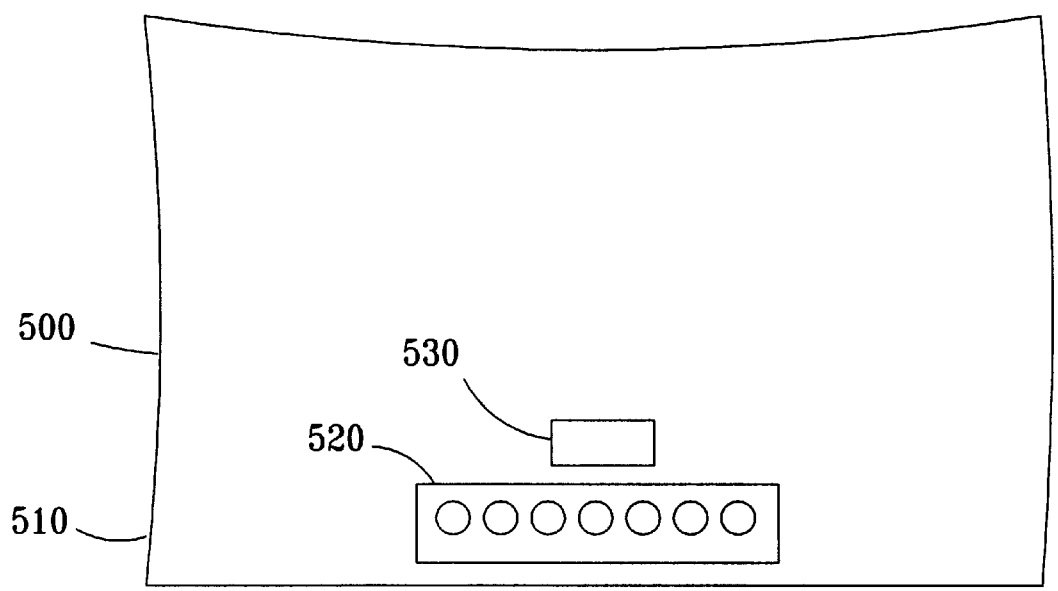
FIG. 10 is a schematic view of a flexible pad having an array of electrode and a mechanical sensor.

Thus, as shown in FIG. 8, the catheter device 10 may be coupled to a processor and interface module 252 and/or to a monitoring device 254 to provide a system 250 for monitoring a fetus 240 during pregnancy and labor. The proximal end 15 of the catheter device 10 may include one or more connectors 19 for connecting to a reusable cable 260, which in turn may be connected to the processor and interface module 252 by a connector 262. The reusable cable 260 may include a platform (not shown in FIG. 8), such as that shown in FIG. 4E, adjacent to the connector 19 that may be attached to a pregnant mother's leg. Alternatively, the reusable cable 260 may include a separate zeroing switch and/or a flush port (not shown), for example, on either end of the reusable cable 260. In a further alternative, the catheter device 10 may be attached directly to the processor and interface module 252.

The reusable cable 260 enables processor circuitry (not shown) in the processor and interface module 252 to be coupled to the pressure transducer (not shown) and/or the array of electrodes 40 for extracting data from the signals. Alternatively, the processor circuitry may be provided internally within the monitoring device 254 along with the other internal electronics therein (not shown), as will be appreciated by those skilled in the art. Preferably, the processor and interface module 252 includes memory and/or processor circuitry for extracting maternal and/or fetal ECG or heart rate from the signals received from the array of electrodes 40 and for obtaining intrauterine pressure data from the pressure transducer.

The processor and interface module 252 may include interface circuitry (not shown) therein for communicating with the monitoring device 254 via one or more cables or other connections. For example, the processor and interface module 252 may produce an output signal, such as a substantially noise-free fetal ECG signal, corresponding to fetal heart rate information obtained from the array of electrodes which may be recognized by the monitoring device. The monitoring device 254 may then record, store and/or display the data in a useful manner, e.g., on a digital display 256 and/or a chart recorder 258. The displayed information may then be used by clinicians to observe the pregnant mother and fetus during the later stages of pregnancy and/or during labor itself.

Turning to FIGS. 3A–3C, a removable insertion guide tube 210 is shown to facilitate insertion of an intrauterine device (not shown in FIGS. 3A–3C), such as the catheter device 10 of FIG. 1. The guide tube 210 is a semi-rigid tubular member 212 having an enclosed distal end 214, an open proximal end 216 including a peel-away tab 218, and one or more notches 220. Preferably, the guide tube 210 includes an enlarged distal portion 222 covered with latex or similar material. An intrauterine device may be pre-inserted into the proximal end 216 until the distal tip of the device is received in the enlarged distal portion 222, and the assembly sterilized, thereby providing a ready-to-use device for substantially sterile introduction into a patient.

With the guide tube 210, the intrauterine device may be introduced into the patient's uterus with enhanced cleanliness and comfort. Once the intrauterine catheter device is in place, the guide tube 210 may be removed and discarded. For example, as shown in FIG. 3A, the guide tube 210 may include notches 220 extending along the length of the tubular member 212 and/or across the distal end 214. To remove the guide tube 210, the tab 218 may be held and drawn proximally, thereby causing the distal tip of the intrauterine device to engage the enlarged distal portion 222 of the guide tube 210. The stress may cause the notches 220 to fail, thereby creating an opening in the distal portion 222 and/or along the tubular member 212. The guide tube 210 may then be withdrawn from the uterus over the intrauterine device and out of the patient's body. Alternatively, instead of the notches 220, other weakened regions or seams may be formed directly in the material of the guide tube 210 or otherwise provided thereon, as will be appreciated by those skilled in the art.

Turning to FIG. 6A, in accordance with another aspect of the present invention, an intrauterine catheter device 310 is shown that includes an array of mechanical sensors 330 for sensing fetal and/or maternal heart rate. The catheter device 310 is an elongate tubular member 312 including a proximal portion (not shown) and a distal portion 314 having a size and shape adapted for insertion into a patient's uterus during labor. The catheter device 310 also preferably includes an array of electrodes 322 and may include a pressure transducer 320, or alternatively may be provided 310 with an array of non-electrode sensors 330 without the array of electrodes 322 (see FIG. 6B).

The array of mechanical sensors 330 may include one or more acoustic sensors spaced apart from one another along the distal portion 314 of the catheter device 310. Such acoustic sensors may be directional, whereupon each acoustic sensor may be located at a different location about the circumference or periphery of the catheter device 310 to obtain acoustical data in a plurality of directions within the uterus. Exemplary acoustic sensors that may be included in the array include a barium titanate (crystal) acoustic sensor, a micro electromechanical acoustic sensor or array of silicon sensors, similar to those made by SiTek, a BEI Company, a phonocardiogram microphone, or an electret condenser microphone cartridge, such as those made by Panasonic, or a miniature audio transducer/sensor.

In a preferred form, the acoustic sensor is a miniature hydrophone device mounted on or in the catheter device 310. Preferably, the hydrophone includes a sleeve of piezo polymer (not shown), e.g. about 3–5 inches in length, which may be provided between inner and outer electrode elements, for example, in a coaxial cable arrangement. Alternatively, a piezoelectric copolymer segment may be provided with internal and external electrodes formed directly onto the copolymer. The segment may take the form of a cylindrical sleeve, a flat panel, e.g. of a substantially square or circular shape, and the like. A hydrophone device may be advantageous over other acoustic sensors because hydrophones may provide consistent acoustical output despite being exposed to water or other fluid and/or to a changing pressure environment.

Returning to FIG. 6A, cables or other leads (not shown) may extend from the array of acoustic sensors 330 and/or from the array of electrodes 322 proximally to the proximal portion (not shown) of the catheter device 310. One or more connectors (not shown) may be provided on the proximal portion for coupling each of the arrays to processor circuitry and/or directly to a monitoring device (not shown). Preferably, the processor circuitry provides an output signal that enables the monitoring device to derive a fetal heart rate and/or maternal heart rate from the data sensed by the array of acoustic sensors 330 in conjunction with the signals obtained from the array of electrodes 322.

For example, the processor circuitry may receive an ECG signal from the array of electrodes 322 and an output signal from the array of acoustic sensors 330. The ECG signal may include ECG activity within the pregnant mother, particularly within her uterus, i.e., corresponding to her heart activity and/or that of the fetus. The output signal from the array of acoustic sensors 330 may correspond to acoustic activity within the uterus, i.e., to the sound of the fetal and maternal heart beat, as well as other random sounds. The processor circuitry may filter "noise," e.g., corresponding to less correlated movements or sounds, from the output signal of the array of acoustic sensors 330. The processor circuitry may then compare the output signal to the ECG signal obtained from the array of electrodes 322 to derive with greater accuracy the desired heart rate or rates.

The processor circuitry may also compare one or both signals to a database stored in memory circuitry associated with the processor circuitry to further facilitate the derivation of heart rate information in the signals. For example, the database may include information on standard maternal and/or fetal heart rates which may be compared to the signals in order to more accurately derive the desired actual heart rate or rates.

Thus, the combination of detecting ECG activity and acoustical activity within the uterus of a pregnant mother is an important feature of the present invention. A catheter device 310, having one or more acoustic sensors 330 and an array of ECG electrodes 322, may be advanced into the uterus, and the acoustic sensor(s) may detect local sounds within the uterus, including the sound of the fetal heart beating, without requiring direct contact with the fetus.

In an alternative embodiment, an external monitoring device (not shown) may be provided that includes an array of ECG electrodes and one or more acoustical sensors. For example, a substantially flexible pad may be provided that may be strapped, secured with an adhesive or otherwise secured to a pregnant mother's abdomen. A lower surface of the pad may include an array of electrodes spaced apart from one another, and one or more acoustic sensors mounted therein that are oriented to detect activity beyond the lower surface. The lower surface may be placed in contact with the pregnant mother's abdomen, thereby enabling detection of ECG and acoustic activity within the uterus. Processor circuitry may be coupled to the array of electrodes and the acoustic sensor(s) to compare their signals and enable monitoring equipment to derive fetal and/or maternal heart rate information with greater certainty than ECG electrodes or acoustic sensors alone. Thus, an entirely external and passive device may be provided that may enhance the detection of fetal and/or maternal heart rate.

In another alternative embodiment, one or more non-acoustic mechanical sensors may be provided on an intrauterine catheter device or on an external monitoring device, in addition to or in place of one or more acoustic sensors. For example, as shown in FIG. 7A, one or more accelerometer sensors 420 may be provided on an intrauterine catheter device 410. Preferably, each accelerometer sensor 420 includes three micro-accelerometers 422, 424, 426 arranged to measure very small changes in movement along three separate orthogonal axes. The micro-accelerometers 422, 424, 426 produce three channels of data, one proportional to the strength of movement in the corresponding axis. Each channel of data may include periodic heartbeat movements of the mother and/or fetus, as well as other less correlated movements, such as random movements or relatively slow physical movements.

Figure 7B:
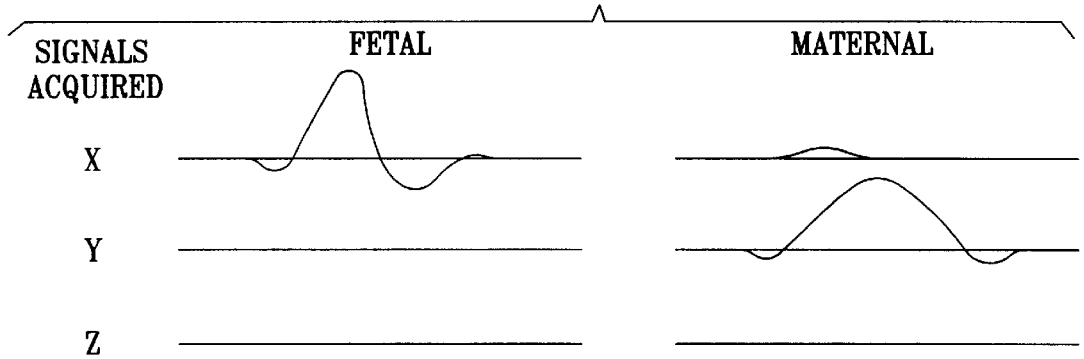
FIG. 7B is a graph showing exemplary heart rate signals that may be acquired by the accelerometer sensor of FIG. 7A.

The accelerometer sensor 420 may provide a ballistogram signal including heart beat information, as shown, for example, in FIG. 7B. Processor circuitry and/or a monitoring device may be coupled to the accelerometer sensor 420 to process the three channels of data from the individual accelerometers 422, 424, 426 to derive the maternal and/or fetal heart rate. The strength of the signals may be sufficiently strong to derive the desired heart rates, or the processor circuitry may process the channels of data in conjunction with signals from acoustic sensors, other mechanical sensors and/or an array of electrodes (not shown) to obtain accurate heart rate information, similar to the acoustic sensors described above.

In still a further alternative, a micro-gyroscope or other mechanical device may be provided that is small enough to be mounted on a catheter device yet is sensitive enough to provide a signal from which maternal and/or fetal heart rates may be derived.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An intrauterine catheter device for monitoring a fetus in utero, comprising:
    an elongate housing having a proximal portion and a distal portion adapted for insertion into a pregnant mother's uterus;
    an array of electrodes on the distal portion adapted to produce an ECG signal; and
    a mechanical sensor on the distal portion, the mechanical sensor being adapted to produce an output signal including a fetal heart rate signal.

2. The intrauterine catheter device of claim 1, wherein the mechanical sensor comprises an acoustic sensor.

3. The intrauterine catheter device of claim 1, wherein the mechanical sensor comprises a hydrophone device.

4. The intrauterine catheter device of claim 1, wherein the mechanical sensor comprises a micro-gyroscope.

5. The intrauterine catheter device of claim 1, wherein the mechanical sensor comprises a micro-accelerometer.

6. The intrauterine catheter device of claim 1, further comprising a pressure transducer on the distal portion for measuring intrauterine pressure.

7. The intrauterine catheter device of claim 1, further comprising one or more connectors on the proximal portion coupled to the array of electrodes and the mechanical sensor.

8. The intrauterine catheter device of claim 1, further comprising processor circuitry for comparing the ECG signal to the output signal of the mechanical sensor to derive fetal heart rate information.

9. A system for monitoring fetal heart rate, comprising:
    an array of electrodes spaced apart from one another;
    one or more mechanical sensors adjacent to the array of electrodes; and
    processor circuitry for comparing an ECG signal produced by the array of electrodes with a signal produced by the one or more mechanical sensors to derive fetal heart rate information.

10. The system of claim 9, further comprising a monitoring device coupled to the processor circuitry for displaying the fetal heart rate information.

11. The system of claim 10, further comprising interface circuitry coupled to the processor circuitry and the monitoring device for communicating therebetween.

12. The system of claim 9, further comprising a pad having a lower surface that may be applied to the abdomen of a pregnant mother, the array of electrodes and the one or more mechanical sensors being located on the lower surface of the pad.

13. The system of claim 9, further comprising an elongate member having a distal portion adapted for insertion into a pregnant mother's uterus, the array of electrodes and the one or more mechanical sensors being located on the distal portion.

14. The system of claim 13, further comprising a pressure transducer on the distal portion.

15. A method for deriving fetal heart rate of a fetus in a pregnant mother's uterus, using a device including an array of electrodes and an acoustic sensor thereon, the method comprising the steps of:
    placing the device adjacent the fetus;
    detecting ECG activity within the uterus with the array of electrodes, the array of electrodes producing an ECG signal corresponding to the ECG activity;
    detecting acoustic activity within the uterus with the acoustic sensor, the acoustic sensor producing an acoustic signal corresponding to the acoustic activity; and
    comparing the ECO signal and acoustic signal to derive the fetal heart rate.

16. The method of claim 15, wherein the device has a distal portion with the array of electrodes and the acoustic sensor thereon, and wherein the distal portion is advanced into the pregnant mother's uterus when the device is placed adjacent the fetus.

17. The method of claim 15, wherein the device is a substantially flexible pad having a lower surface with the array of electrodes and the acoustic sensor thereon, and wherein the lower surface is placed against the abdomen of the pregnant mother when the device is placed adjacent the fetus.

18. The method of claim 15, comprising the additional step of comparing the ECG signal and acoustic signal to derive a maternal heart rate of the pregnant mother.

19. The method of claim 15, comprising the additional step of displaying the fetal heart rate on a monitoring device.

20. An intrauterine catheter device for monitoring a fetus during labor, comprising:

an elongate housing having a proximal portion and a distal portion adapted for insertion into a pregnant mother's uterus;

a reference electrode on the distal portion; and an array of active electrodes spaced apart from one another on the distal portion, wherein the array of active electrodes includes a bipolar pair of electrodes.

21. The intrauterine catheter device of claim 20, wherein the array of active electrodes comprises a plurality of electrodes spaced apart axially from one another.

22. An intrauterine catheter device for monitoring a fetus during labor, comprising:

an elongate housing having a proximal portion and a distal portion adapted for insertion into a pregnant mother's uterus, a reference electrode on the distal portion; and an array of active electrodes spaced apart from one another on the distal portion, wherein the array of active electrodes comprises a pair of electrodes provided back-to-back from one another.

23. The intrauterine catheter device of claim 20, further comprising a pressure transducer on the distal portion.

24. The intrauterine catheter device of claim 20, further comprising processor circuitry coupled to the array of active electrodes and the reference electrode for deriving fetal heart rate information from a signal produced by the array of active electrodes.

25. An intrauterine catheter device for monitoring a fetus during labor, comprising:

an elongate housing having a proximal portion and a distal portion adapted for insertion into a pregnant mother's uterus, and including first and second lumens extending between the proximal and distal portions;

a differential pressure transducer on the distal portion, the transducer having a front side exposed on the distal portion, and a back side disposed within the distal portion, the first and second lumens being in communication with the front and back sides, respectively; and a zeroing switch on the proximal portion of the housing, the zeroing switch being adjustable between first and second positions, whereby in the first position the second lumen is in communication with external atmospheric pressure, and whereby in the second position the second lumen is in communication with the first lumen.

26. The intrauterine catheter device of claim 25, further comprising one or more mechanical sensors on the distal portion.

27. The intrauterine catheter device of claim 25, further comprising an array of ECG electrodes spaced apart from one another on the distal portion.

28. The intrauterine catheter device of claim 25, further comprising a third lumen extending between the proximal and distal portions, the third lumen being connected to the first lumen at a location proximate to the front side of the pressure transducer.

29. The intrauterine catheter device of claim 28, wherein the zeroing switch is adjustable to a third position such that the first lumen is in communication with a port on the zeroing switch, the port being connectable to a source of pressure for forcing fluid from the first lumen.

30. A device for monitoring a fetus in utero, comprising:

a flexible pad having a lower surface for contacting a pregnant mother's abdomen;

an array of electrodes on the lower surface adapted to produce an ECG signal, one or more mechanical sensors on the lower surface adapted to produce an output signal including a fetal heart rate signal; and processor circuitry for comparing the ECG signal to the output signal of the mechanical sensors to derive fetal heart rate information.

31. The device of claim 30, wherein the mechanical sensors comprises an acoustic sensor.

* * * * *